United States Patent [19]

Persson et al.

[11] Patent Number: 5,760,022
[45] Date of Patent: Jun. 2, 1998

[54] PHARMACEUTICAL COMPOSITION WITH IMPROVED BIOAVAILABILITY OF INOSITOL PHOSPHATE

[75] Inventors: Lars Persson, Hässleholm; Torgny Gustafsson; Nicola Rehnberg, both of Perstorp, all of Sweden

[73] Assignee: Perstorp AB, Perstorp, Sweden

[21] Appl. No.: 676,238

[22] PCT Filed: Jan. 24, 1995

[86] PCT No.: PCT/SE95/00064

§ 371 Date: Jul. 17, 1996

§ 102(e) Date: Jul. 17, 1996

[87] PCT Pub. No.: WO95/19775

PCT Pub. Date: Jul. 27, 1995

[30] Foreign Application Priority Data

Jan. 25, 1994 [SE] Sweden ................... 9400202

[51] Int. Cl.⁶ ................................. A61K 31/66
[52] U.S. Cl. ............... 514/103; 514/109; 514/143; 514/144; 514/148; 514/546; 514/547; 514/946
[58] Field of Search ........................ 514/103, 109, 514/143, 144, 148, 546, 547, 946

[56] References Cited

U.S. PATENT DOCUMENTS 4,969,611  11/1990  Katagiri et al. .
4,997,761   3/1991  Jett-Tilton .................... 435/240.2
5,082,833   1/1992  Shamsuddin .................... 514/143

FOREIGN PATENT DOCUMENTS 0 179 439   4/1986   European Pat. Off. .
0 342 956  11/1989   European Pat. Off. .
0 349 143   1/1990   European Pat. Off. .
    7873M   4/1970   France .
60-146808   8/1985   Japan .

OTHER PUBLICATIONS

Chemical Abstracts, vol. 102, No. 1, Abstract No. 6465b, published Jan. 7, 1985.
Sekine et al., "Improvement of Bioavailability of Poorly Absorbed Drugs. I. Effect of Medium Chain Glyceride Base on the Rectal Absorption of Cefmetazole Sodium in Rats", *J. Pharm. Dyn.* 7:856–863 (1984).
Li et al., Synergistic Activation of Retinal Capillary Pericyte Proliferation in Culture by Inositol Triphosphate and Diacylglycerol, *Exp. Eye Res.*, 44:29–35 (1987).

*Primary Examiner*—Rebecca Cook
*Attorney, Agent, or Firm*—Scully, Scott, Murphy & Presser

[57] ABSTRACT

The invention relates to an inositol phosphate containing pharmaceutical composition which comprises an aliphatic ester or ether for improvement of the bioavailability of the inositol phosphate in mammals including man at non-parenteral administration. The invention also covers the use of at least one aliphatic ester or ether compound for the preparing of an inositol phosphate containing medicament with improved bioavailability of inositol phosphate in mammals including man at non-parenteral administration.

21 Claims, No Drawings

PHARMACEUTICAL COMPOSITION WITH IMPROVED BIOAVAILABILITY OF INOSITOL PHOSPHATE

This is a 371 of PCT/SE95/00064 filed Jan. 24, 1995.

The present invention relates to an inositol phosphate containing pharmaceutical composition with improved bioavailability of inositol phosphate and the use of at least one aliphatic ester or ether compound with the formula I or II below for the preparing of an inositol phosphate containing medicament with improved bioavailability of inositol phosphate at non-parenteral administration.

Hydrophilic and ionized drugs most often encounter rather poor penetration of the epithelial barriers to the capillaries of the portal circulation as most of this type of substances are transported by passive diffusion. Inositol phosphates belong to this group.

Normally it is the unionized fraction of the drug that partition across the lipid membranes and this fraction is most often small over the pH-range encountered in the gastrointestinal tract.

It is known from the literature, for example M. Sekine et al., (1984), J.Pharm. Dyn. 7, 856–863 that a combination of specific glyceryl-containing compounds and some antibiotics render an improved absorption of the antibiotic after rectal administration. However the amount of the glyceryl containing compound is very high resulting in an inconvenient formulation with potential side effects.

Nothing has been described in the literature about the use of an aliphatic ester or ether compound with formula I or II together with inositol phosphate for improvement of the bioavailability of the inositol phosphate.

At oral administration the properties of inositol phosphates per se result in limitations in respect of the uptake of the compounds from the intestine. In order to optimize the effect of these substances in the body it is desirable that as large a portion as possible of the added amount can be utilized effectively. Thereby the added amount can be reduced which is advantageous for the patient for example when the drug D-myo-inositol-1,2,6-trisphosphate ($IP_3$) is used.

According to the present invention it has now quite surprisingly been possible to meet the above desire and bring about an inositol phosphate containing pharmaceutical composition which comprises an aliphatic ester or ether compound with formula I or II below for improvement of the bioavailability of the inositol phosphate in mammals including man at non-parenteral administration.

The expression bioavailability stands for the measurement of how large a portion of an administered drug that occurs in the blood stream when the way of administration of the drug is non-parenteral. The term thus shows the amount of the drug that has been able to penetrate membrane barriers after for example oral administration, topical administration or intraperitoneal administration.

The aliphatic ester or ether compound with 3 to 18 carbon atoms can be defined by the formula I.

$CH_2OR_1CHOR_2CH_2OR_3$ wherein $R_1$, $R_2$ and/or $R_3$ independently are i) hydrogen;

ii) a straight or branched alkyl with 1 to 15 carbon atoms such as methyl, ethyl, propyl, butyl, pentyl, hexyl, heptyl, octyl, nonyl, decyl, undecyl, dodecyl, tridecyl, tetradecyl and pentadecyl;

iii) a cycloalkyl with 3 to 15 carbon atoms such as cyclopropyl, cyclopentyl and/or cyclohexyl;

iv) an alkenyl with 2 to 14 carbon atoms such as vinyl, allyl, propenyl, octadienyl, decenyl, dodecenyl and/or tetradecenyl;

v) a cycloalkenyl with 5 to 14 carbon atoms such as cyclopentenyl, cyclopentadienyl, cyclohexenyl and/or cyclohexadienyl;

vi) a straight or branched acyl radical of a saturated aliphatic carboxylic acid with 1 to 15 carbon atoms such as formyl, acetyl, propionyl, butyryl, isobutyryl, valeryl, hexanoyl, heptanoyl, octanoyl, nonanoyl, decanoyl, pivaloyl, lauroyl and/or myristoyl;

vii) a straight or branched acyl radical of an unsaturated aliphatic carboxylic acid with 1 to 15 carbon atoms such as acryloyl, propiolyl, oleoyl, maleoyl, fumaroyl and/or citraconoyl;

viii) an acyl radical of a saturated cyclic carboxylic acid such as cyclopentanoyl or ix) an acyl radical of an unsaturated cyclic carboxylic acid such as furoyl.

The above groups (ii) to (ix) are unsubstituted or substituted with hydroxy; oxo; alkoxy; carboxy; esterified carboxy; amine, substituted amine; acyloxy or acylamine.

In one preferred embodiment of the invention where a compound with formula I is used $R_1$ and $R_2$ are i) hydrogen or ii) a straight or branched alkyl selected from the group of methyl, ethyl, propyl, butyl, pentyl, hexyl, heptyl and/or octyl and $R_3$ is i) a straight or branched alkyl selected from the group of butyl, hexyl, octyl and/or decyl or ii) a straight or branched acyl radical of a saturated aliphatic carboxylic acid with 1 to 15 carbon atoms such as butanoyl, hexanoyl, octanoyl and/or decanoyl.

Preferred compounds in this group are 1,2-dihydroxypropylbutanoate, 2,3-dihydroxypropylbutanoate, 1,3-dipropylbutanoate, hydroxypropylbutanoate, 1,2-dihydroxypropyl-hexanoate, 2,3-dihydroxypropylhexanoate, 1,3-dihydroxypropylhexanoate, 1,2-dihydroxypropyloxtanoate, 1,3-dihydroxypropyloctanoate, 2,3-dihydroxypropyloctanoate, 1,2-dihydroxypropyldecanoate, 1,3-dihydroxypropyloctanoate and 2,3-dihydroxypropyldecanoate.

The aliphatic ester or ether compound can also have the following formula:

a) $CH_2OR1CH_2OR_2$, b) $CH_3CHOR_1CH_2OR_2$, c) $CH_2OR_1(CHOR_2)_nCH_2OR_3$ wherein n is an integer between 1 and 4 or d) $C((CH_2OR_1)_2CH_2OR_2CH_2OR_3)$ wherein $R_1$, $R_2$ and/or $R_3$ independently are as defined above.

In one embodiment of this type of the invention where the compound has the formula (a) or (b), $R_1$ and/or $R_2$ are i) hydrogen;

ii) a straight or branched alkyl selected from the group of methyl, ethyl, propyl, butyl, pentyl, hexyl, heptyl and/or octyl or iii) a straight or branched acyl radical of a saturated, aliphatic carboxylic acid with 1 to 15 carbon atoms, such as butanoyl, hexanoyl, octanoyl and/or decanoyl.

In another embodiment of this type of the invention where the compound has the formula (c) or (d), $R_1$ and/or $R_2$ are i) hydrogen;

ii) a straight or branched alkyl selected from the group of methyl, ethyl, propyl, butyl, pentyl, hexyl, heptyl and/or octyl or iii) a straight or branched acyl radical of a saturated, aliphatic carboxylic acid with 1 to 15 carbon atoms, such as butanoyl, hexanoyl, octanoyl and/or decanoyl and $R_3$ is i) a straight or branched alkyl selected from the group of butyl, hexyl, octyl and/or decyl or ii) a straight or branched acyl radical of a saturated aliphatic carboxylic acid with 1 to 15 carbon atoms such as butanoyl, hexanoyl, octanoyl and/or decanoyl.

The aliphatic ester or ether compound can also have the formula II, $R_4COOR_5$ wherein $R_4$ is i) hydrogen;

ii) a straight or branched alkyl with 1 to 15 carbon atoms such as methyl, ethyl, propyl, butyl, pentyl, hexyl, heptyl, octyl, nonyl, decyl, undecyl, dodecyl, tridecyl, tetradecyl and/or pentadecyl;

iii) a cycloalkyl with 3 to 15 carbon atoms such as cyclopropyl, cyclopentyl and/or cyclohexyl or iv) an alkenyl with 2 to 14 carbon atoms such as vinyl, allyl, propenyl, octadienyl, decenyl, dodecenyl and/or tetradecenyl;

the above groups (i) to (iv) being unsubstituted or substituted with hydroxy; oxo; alkoxy; carboxy; esterified carboxy; amine; substituted amine; acyloxy or acylamine, and wherein $R_5$ is i) hydrogen;

ii) a cation such as sodium and/or potassium or iii) $R_4$ as defined above

In one preferred embodiment of the invention where the compound is used, $R_4$ is selected from the group consisting of propyl, butyl, pentyl, hexyl, heptyl, octyl, nonyl and decyl and $R_5$ is i) hydrogen;

ii) a cation such as sodium and/or potassium or iii) a lower alkyl such as methyl, ethyl or propyl.

According to the invention the amount of the aliphatic ester or ether compound in the composition can be fairly low. From the view of the patient this is very favourable as no side effects or other pharmacological effects from these compounds are observed.

One way of expressing the amount of the compound needed is the weight per kg body weight. The final formulation can contain 0.2 to 200 mg of the compound per kg body weight, for example preferably 0.2 to 50 mg of the compound per kg body weight and most preferably 0.2 to 20 mg of the compound per kg body weight.

Another way of expressing the amount of the compound needed is the weight per weight of active substance i.e. the amount of inositol phosphate. The final formulation can contain 0.1 to 100 mg of the compound per mg inositol phosphate, for example preferably 0.5 to 10 mg of the compound per mg inositol phosphate and most preferably 0.5 to 5 mg of the compound per mg inositol phosphate.

The expression inositol phosphate comprises phosphate or phosphates of different isomers of inositol for example myo-inositol, allo-inositol, cis-inositol, chiro-inositol, scyllo-inositol, muco-inositol, neo-inositol or epi-inositol. Most often the inositol isomer is myo-inositol.

The degree of phosphorylation can vary between one phosphate group/inositol moiety to six phosphate groups/inositol moiety.

Preferably inositol trisphosphate isomers are used according to the invention and most preferably D-myo-inositol-1, 2,6-trisphosphate ($IP_3$) is used.

According to the invention the inositol phosphate is most often present in an salt form or in a form where only a few of the negative charges are protonated. The salt can contain one or more cations in different combinations. Examples of cations are sodium and potassium ions.

The pharmaceutical composition according to the invention may be administered orally, topically, rectally or by inhalation spray in dosage forms or formulations comprising conventional, non-toxic pharmaceutically acceptable carriers, adjuvants and vehicles. The preferred administration route is oral administration.

The pharmaceutical composition for oral use can be present in different forms such as capsules, granules, tablets, troches, lozenges, aqueous suspensions, dispensible powders, emulsions, syrups or elixirs. When the composition is present in liquid form capsules are preferably utilized. At the use of granules, these preferably have a size of 0.15-2 mm. Either the granules can consist of the pharmaceutical composition per se or of the composition and suitable fillers. When the pharmaceutical composition is used in a tablet form, the tablets can have a weight of 50-1500 mg, preferably 50-800 mg and most preferably 100-500 mg.

Formulations for oral use include tablets which contain the active ingredient in a mixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

For the rectal application of the composition of this invention, typical dosage forms include suppositories, rectal gelatin capsules (solutions and suspensions), and enemas or micro-enemas (solutions and suspensions). Thus, in a typical suppository formulation, any one of the compounds of this invention is combined with any pharmaceutically acceptable suppository base such as cocoa butter, esterified fatty acids, glycerinated gleatin, and various water-soluble or dispersible bases like poly-ethylene glycols and polyoxyethylene sorbitan fatty acid ester. Various additives like salicylates or surfactant materials may be incorporated.

For topical use, creams, ointments, gels, solutions or the like containing the compositions are employed according to methods recognized in the art.

Naturally, the therapeutic dosage range for the compounds of the present invention will vary with the size and needs of the patient and the particular pain or disease symptom being treated.

The administration of the pharmaceutical composition according to the invention can be in a combined dosage form or in separate dosage forms.

As mentioned above the invention also relates to the use of at least one aliphatic ester or ether compound with formula I or II for the preparing of an inositol phosphate containing medicament with improved bioavailability of inositol phosphate in mammals including man at non-parenteral administration.

As mentioned above the aliphatic ester or ether compound can have the following formulas:

A. $CH_2OR_1CHOR_2CH_2OR_3$
B. $CH_2OR_1CH_2OR_2$
C. $CH_3CHOR_1CH_2OR_2$
D. $CH_2OR_1(CHOR_2)_nCH_2OR_3$
E. $C((CH_2OR_1)_2 CH_2OR_2CH_2OR_3)$
F. $R_4COOR_5$ wherein $R_1$, $R_2$, $R_3$, $R_4$, $R_5$ and n are as defined above.

Preferably the compound is selected from the group of dihydroxypropyl butanoate, dihydroxypropyl hexanoate, dihydroxypropyl octanoate and dihydroxypropyl decanoate.

Preferably the inositol phosphate is inositol trisphosphate and most preferably the inositol trisphospate is D-myo-inositol-1,2,6-trisphosphate.

Another embodiment of the invention relates to pharmaceutical compositions comprising a aliphatic ester or ether compound with anyone of formulas A–F above and other phosphorus-containing inositol derivatives. For example different types of phosphonates of inositol encounter the need of improved bioavailability after non-parenteral administration. Still another embodiment of the invention relates to pharmaceutical compositions comprising an aliphatic ester or ether compound with anyone of formulas A–F and derivatives of inositol phosphates and inositol phosphonates. The derivatives could be compounds where the phosphate or phosphonate group or groups are further esterified or compounds where the hydroxyl groups on the inositol moiety are etherified or esterified, such as alkanoyl and carbamoyl derivatives. A further embodiment of the invention is related to compositions comprising an aliphatic ester or ether compound with anyone of formulas A–F above and inositol derivatized with other charged groups such as carboxyl and sulphonyl. The aliphatic ester or ether compound used in these embodiments belong to the same groups as disclosed above.

The invention also relates to the improvement of the penetration of cellmembranes in a wider aspect than in the above definition of bioavailability. Under certain circumstances there is a need to be able to obtain an improved ability of different isomers of inositol, phosphates or derivatives thereof to cross cell membranes.

Such an example is when it is desirable to let the inositol phosphate or its derivative influence different intracellular metabolic pathways. This can be the case for example when new drugs based on inositolphosphate compounds are being developed. Another example is when the knowledge of different cellular signal systems is further explored. For example it is known that some isomeric structures of inositol phosphates exist intracellularly. In many cases it is advantageous to be able to add these substances from the extracellular space in order to clarify in more detail how they effect the behaviour of the cells. This knowledge can then be used in order to develop agonistic or antagonistic compounds effecting the cellular response.

The combination of an aliphatic ester or ether compound as disclosed above and an inositol phosphate or its derivative will facilitate the penetration across cellular membranes.

Another area is when it is desirable to facilitate the transport of nucleosides across cellular membranes. The combination of an aliphatic ester or ether compound as described above and a nucleoside will enhance the penetration of cellular membranes.

Furthermore the invention can be used for the pharmaceuticals which suffer from low bioavailability due to the same reasons as inositol phosphates and their derivatives.

One such application is a pharmaceutical composition comprising an aliphatic ester or ether compound as defined above and a bisphosphonate or a derivative thereof useful for the treatment of bone disorders such as osteoporosis and other conditions characterized by abnormal calcium metabolism.

The bisphosphonate or the derivative thereof could be selected from the group of hydroxy ethane bisphosphonate, amino ethane bisphosphonate, dichloromethylene bisphosphonate, methylene bisphosphonate, and preferably:

1-hydroxy-3-aminopropane-1,1-bisphosphonate
1-hydroxy-6-aminohexane-1,1-bisphosphonate
4-amino-1-hydroxybutylidene-1,1-bisphonate N-methyl-4-amino-1-hydroxy butylidene-1,1-bisphosphonate
3-amino-1-hydroxypropylidene-1,1-bisphosphonate
1-hydroxy ethylidene-1,1-bisphosphonate 4-(hydroxy methylene-bisphosphonate)piperidine Another application is a pharmaceutical composition comprising an aliphatic ester or ether compound as defined above and a bisphosphonate or a derivative thereof useful for the treatment of cardiovascular conditions such as increased cholesterol levels and atherosclerosis. The bisphosphonate or the derivative thereof could be selected from the group of alkyl bisphosphonate, alkenyl bisphosphonates, alkynyl bisphosphonates, phenyl alkyl bisphosphonates and phenoxyalkyl bisphosphonates.

Still another application is a pharmaceutical composition comprising an aliphatic ester or ether compound as defined above and a specific bisphosphonate useful as anti-microbial agents. The bisphosphonate in this application is selected from the group of alkyl ethenylidene, bisphosphonates such as tetraisopropyl ethenylidene bisphosphonate and diethyl dibutyl ethenylidene bisphosphonate. The invention can also be used for other pharmaceuticals suffering from low bioavailability such as antiviral agents. One such application is a pharmaceutical composition comprising an aliphatic ester or ether compound as defined above and a charged phosphorus-containing pharmaceutical or a biologically active compound such as:

phosphonoformiate,
phosphonoacetate,
3-azido thymidine-5-phosphate,
9-(2-phosphonyl methoxy ethyl) adenine,
S-9-(3-hydroxy-2-phosphonyl methoxy propyl) adenine/cytosine,
2', 3'-didehydro-2,3-dideoxy thymidine,
(2R, 5R)-9-(2,5-dihydro-5-phosphonomethoxyl)-2-furanyl adenosine and derivatives thereof. The compositions are useful for the treatment of CMV-infections, HIV-infections, herpes simplex and hepatitis B.

The invention can also be used for other pharmaceuticals and biologically active compounds with low and limited bioavailability such as phosphorylated and phosphonylated sugar residues, for example hydroxy phosphonyl glucoseamine derivatives, purine and pyrimidine nucleotides and derivatives thereof for example 2'-deoxy-5-fluorouridine 5'-phosphate and oligonucleotides and derivatives thereof. Those skilled in the art will realize that the list of compounds is not exhaustive and the invention is also applicable to other pharmaceuticals and biologically active compounds comprising a phosphate or phosphonate moiety.

Preferably, the above aliphatic ester or ether compounds contain 3 to 18 carbon atoms.

In some embodiments of the invention also an aromatic ester or ether compound with 3 to 18 carbon atoms could be contemplated to be utilized.

The invention will be explained further in connection with the embodiment examples below, however without limiting it thereto.

Example 1 shows the manufacturing of a pharmaceutical composition comprising a mixture of dihydroxypropyl octanoate and $IP_3$. Example 2 and 3 illustrate the determination of the bioavailability of two different dihydroxypropyl esters and $IP_3$ after oral administration.

Example 1

The pentasodium salt of D-myo-inositol-1,2,6-trisphosphate ($IP_3$), 2.0 g, was mixed with 4.1 g of 2,3-dihydroxypropyl octanoate to form an composition consisting of 4 moles of the 2,3-dihydroxypropyl octanoate compound/$IP_3$-moiety.

Example 2

The bioavailability of a composition comprising a mixture of 2,3-dihydroxypropyl octanoate and D-myo-inositol-1,2,6-trisphosphate ($IP_3$) (obtained according to Example 1) after oral administration was determined in an experiment with pigs. Five pigs were given an intravenous injection of the sodium salt of $IP_3$ and blood samples were collected 0.25 hr, 0.5 hr, 1 hr, 1.5 hrs, 2 hrs, 4 hrs, 6 hrs and 8 hrs after the injection. The blood samples were assayed for the content of $IP_3$ and these measurements were used for the calculation of the reference data as 100% of the substance is introduced into the blood stream after an intravenous injection. Another five pigs were given the composition comprising the mixture of 2,3-dihydroxypropyl octanoate and $IP_3$ as an intraduodenal dosing. The animals were treated with Atropin and anaesthetized with Hypnodil®/Sedaperone® whereafter a laparotomy was carried out. Blood samples were collected at the time intervals mentioned above and the concentration of $IP_3$ was determined in each sample. By calculating the area under the curve (AUC) from a graph where the concentration versus time is shown and comparing the obtained value with a similar calculation from the data after intravenous injection of the substance the bioavailability for this specific formulation is obtained.

Still another five pigs were given the penta-sodium salt of $IP_3$ orally. Blood samples were collected at the same time intervals as above and the concentration of $IP_3$ was determined. Following a similar procedure the AUC was determined.

The following concentrations of $IP_3$ were obtained after intravenous injection of the sodium salt, after oral administration of the composition comprising 2,3-dihydroxypropyl octanoate and $IP_3$ and after oral administration of the sodium salt respectively.

| time | intravenous, injection, sodium salt of $IP_3$ | conc $IP_3$ (µM) oral formulation, composition comprising 2,3-dihydroxy-propyl octanoate and $IP_3$ | oral formulation, sodium salt of $IP_3$ |
|---|---|---|---|
| 0 | 0 | 0 | 0 |
| 0.25 | 53.7 | 24.0 | — |
| 0.5 | 40.0 | 20.2 | 0.6 |
| 1.0 | 21.6 | 13.2 | 0.5 |
| 1.5 | 12.1 | 11.2 | 0.5 |
| 2.0 | 9.3 | 8.6 | 0.6 |
| 4.0 | 2.6 | 2.8 | 0.4 |
| 6.0 | 1.1 | 1.1 | 0.4 |
| 8.0 | 0.6 | 0.5 | 0 |
| Normalized AUC (%) | 100 | 58 | 3 |

The bioavailability of $IP_3$ at the use of the oral formulation consisting of 2,3-dihydroxypropyl octanoate and $IP_3$ was 58%. Irritancy test showed no toxic effects on the intestinal barriers.

Example 3

The bioavailability of a composition comprising a mixture of 2,3-dihydroxypropyl butanoate and $IP_3$ after oral administration was determined with a method similar to the description in Example 2. Five pigs were given an intravenous injection of the penta-sodium salt of $IP_3$ while another five animals were given a formulation consisting of a mixture of 2,3-dihydroxypropyl butanoate and $IP_3$ as and intraduodenal dosing. Still another group of five pigs were given the penta-sodium salt of $IP_3$ orally. Blood samples were collected and the concentration of $IP_3$ were determined.

The following concentrations of $IP_3$ were obtained after intravenous injection of the sodium salt, after oral administration of the composition comprising 2,3-dihydroxypropyl butanoate and $IP_3$ and after oral administration of the sodium salt respectively.

| time (hrs) | intravenous, injection sodium salt of $IP_3$ | conc $IP_3$ (µM) oral formulation, composition comprising 2,3-dehydroxy propylbutanoate and $IP_3$ | oral formulation, sodium salt of $IP_3$ |
|---|---|---|---|
| 0 | 0 | 0 | 0 |
| 0.25 | 53.7 | 2.8 | — |
| 0.5 | 40.0 | 4.2 | 0.6 |
| 1.0 | 21.6 | 4.0 | 0.5 |
| 1.5 | 12.1 | 3.8 | 0.5 |
| 2.0 | 9.3 | 1.7 | 0.6 |
| 4.0 | 2.6 | 0.8 | 0.4 |
| 6.0 | 1.1 | 0.6 | 0.4 |
| 8.0 | 0.6 | 0.1 | 0 |
| Normalized AUC (%) | 100 | 23 | 3 |

The bioavailability of $IP_3$ at the use of the oral formulation consisting of the 2,3-dihydroxypropyl butanoate and $IP_3$ was 23%. Irritancy test showed no toxic effects on the intestinal barriers.

We claim:

1. A non-parenteral pharmaceutical composition which comprises a mixture of at least one inositol phosphate and an aliphatic ester or ether having the formula $CH_2OR_1CHOR_2CH_2OR_3$, in the amount effective to improve the bioavailability of said inositol phosphate wherein $R_1$, $R_2$ and $R_3$ independently are i) hydrogen;

ii) a straight or branched alkyl having 1 to 15 carbon atoms;

iii) a cycloalkyl having 3 to 15 carbon atoms;

iv) an alkenyl having 2 to 14 carbon atoms;

v) a cycloalkenyl having 5 to 14 carbon atoms;

vi) a straight or branched acyl radical of a saturated aliphatic carboxylic acid having 1 to 15 carbon atoms;

vii) a straight or branched acyl radical of an unsaturated aliphatic carboxylic acid having 1 to 15 carbon atoms;

viii) an acyl radical of a saturated cyclic carboxylic acid or ix) an acyl radical of an unsaturated cyclic carboxylic acid, wherein groups (ii) to (ix) are unsubstituted or substituted with hydroxy; oxo; alkoxy; carboxy; esterified carboxy; amino; acyloxy; or acylamine.

2. A composition according to claim 1 wherein $R_1$, $R_2$ and $R_3$ are independently hydrogen, or a straight or branched acyl radical of a saturated aliphatic carboxylic acid having 1 to 15 carbon atoms.

3. A composition according to claim 2 wherein $R_1$ and $R_2$ are hydrogen and $R_3$ is a straight or branched acyl radical of a saturated aliphatic carboxylic acid having 1 to 15 carbon atoms.

4. A composition according to claim 1 wherein the inositol phosphate is at least one isomer of inositol triphosphate.

5. A composition according to claim 4 wherein said isomer of inositol triphosphate is D-myo-inositol-1,2,6-triphosphate.

6. A composition according to claim 4 wherein the inositol triphosphate is present in salt form.

7. A composition according to claim 5 wherein the inositol triphosphate is present in salt form.

8. A composition according to claim 5 in capsule, tablet or granulated form.

9. A composition according to claim 5 in a combined dosage form.

10. A composition according to claim 1 wherein $R_1$, $R_2$ and $R_3$ are independently methyl, ethyl, propyl, butyl, pentyl, hexyl, heptyl, octyl, nonyl, decyl, undecyl, dodecyl, tridecyl, tetradecyl, pentadecyl, cyclopropyl, cyclopentyl, cyclohexyl, vinyl, allyl, propenyl, octadienyl, decenyl, dodecenyl, tetradecenyl, cyclopentenyl, cyclopentadienyl, cyclohexenyl, cyclohexadienyl, formyl, acetyl, propionyl, butyryl, isobutyryl, valeryl, hexanoyl, heptanoyl, octanoyl, nonanoyl, decanoyl, pivaloyl, lauroyl, myristoyl, acryloyl, propiolyl, oleoyl, maleoyl, fumaroyl, citraconoyl, cyclopentanoyl or furoyl.

11. A composition according to claim 10 wherein $R_1$, $R_2$ and $R_3$ are independently hydrogen, formyl, acetyl, propionyl, butyryl, isobutyryl, valeryl, hexanoyl, heptanoyl, octanoyl, nonanoyl, decanoyl, pivaloyl, lauroyl or myristoyl.

12. A composition in accordance with claim 3 wherein $R_3$ is formyl, acetyl, propionyl, butyryl, isobutyryl, valeryl, hexanoyl, heptanoyl, octanoyl, nonanoyl, decanoyl, pivaloyl, lauroyl or myristoyl.

13. A composition according to claim 12 wherein $R_1$ and $R_2$ are hydrogen and $R_3$ is octanoyl.

14. A non-parenteral pharmaceutical composition which comprises a mixture of at least one inositol phosphate and an aliphatic ester having the formula $R_4COOR_5$, in an amount effective to improve the bioavailability of said inositol phosphate, wherein $R_4$ is i) hydrogen;

ii) a straight or branched alkyl having 1 to 15 carbon atoms;

iii) a cycloalkyl having 3 to 15 carbon atoms; or iv) an alkenyl with 2 to 14 carbon atoms, wherein groups (ii) to (iv) are unsubstituted or substituted with hydroxy; oxo; alkoxy; carboxy; esterified carboxy; amino; acyloxy or acylamine; and $R_5$ is $R_4$ or a cation.

15. A composition in accordance with claim 14 wherein $R_4$ is hydrogen, methyl, ethyl, propyl, butyl, pentyl, hexyl, heptyl, octyl, decyl, undecyl, dodecyl, tridecyl, tetradecyl, pentadecyl, cyclopropyl, cyclopentyl, cyclohexyl, vinyl, allyl, propenyl, octadienyl, decenyl, dodecenyl or tetradecenyl, with the proviso that, except for hydrogen, the above meanings of $R_4$ are unsubstituted or substituted with hydroxy, oxo, alkoxy, carboxy, esterified carboxy, amino, acyloxy or acylamine; and $R_5$ is $R_4$, sodium or potassium.

16. A composition in accordance with claim 14 wherein the inositol phosphate is at least one specific isomer of inositol triphosphate.

17. A composition according to claim 15 wherein the inositol phosphate is at least one specific isomer of inositol triphosphate.

18. A composition according to claim 16 wherein the inositol triphosphate is D-myo-inositol-1,2,6-triphosphate.

19. A composition according to claim 17 wherein the inositol triphosphate is D-myo-inositol-1,2,6-triphosphate.

20. A composition according to claim 17 wherein the inositol triphosphate is present in salt form.

21. A composition according to claim 19 in capsule, tablet or granulated form.

\* \* \* \* \*